US012239621B2

(12) United States Patent
Saito et al.

(10) Patent No.: US 12,239,621 B2
(45) Date of Patent: Mar. 4, 2025

(54) PREVENTION OF KIDNEY INJURY INDUCED BY HEMOLYTIC REACTION

(71) Applicants: Niigata University, Niigata (JP); Denka Company Limited, Tokyo (JP)

(72) Inventors: Akihiko Saito, Niigata (JP); Sawako Goto, Niigata (JP); Yoshiaki Hirayama, Tokyo (JP)

(73) Assignees: Niigata University, Niigata (JP); Denka Company Limited, Tokyo (JP)

( * ) Notice: Subject to any disclaimer, the term of this patent is extended or adjusted under 35 U.S.C. 154(b) by 0 days.

(21) Appl. No.: 18/247,412

(22) PCT Filed: Mar. 8, 2022

(86) PCT No.: PCT/JP2022/010031
§ 371 (c)(1),
(2) Date: Mar. 30, 2023

(87) PCT Pub. No.: WO2022/191193
PCT Pub. Date: Sep. 15, 2022

(65) Prior Publication Data
US 2023/0390229 A1 Dec. 7, 2023

(30) Foreign Application Priority Data
Mar. 12, 2021 (JP) ................. 2021-040083

(51) Int. Cl.
A61K 31/194 (2006.01)
A61K 9/00 (2006.01)
A61P 13/12 (2006.01)

(52) U.S. Cl.
CPC .......... *A61K 31/194* (2013.01); *A61K 9/0019* (2013.01); *A61P 13/12* (2018.01)

(58) Field of Classification Search
CPC ............................ A61K 31/198; A61K 31/194
See application file for complete search history.

(56) References Cited

U.S. PATENT DOCUMENTS

| 9,216,185 | B2 | 12/2015 | Tejedor Jorge et al. | |
| 11,304,919 | B2* | 4/2022 | Saito | A61P 13/12 |
| 2006/0009496 | A1 | 1/2006 | Oates et al. | |
| 2016/0271164 | A1 | 9/2016 | Zager et al. | |
| 2016/0324813 | A1 | 11/2016 | Saito et al. | |
| 2016/0376322 | A1 | 12/2016 | Krishna et al. | |
| 2017/0218035 | A1 | 8/2017 | Mclean et al. | |
| 2019/0262321 | A1 | 8/2019 | Peters et al. | |
| 2020/0254053 | A1 | 8/2020 | Krishna et al. | |
| 2021/0228522 | A1* | 7/2021 | Saito | A61K 9/0019 |

OTHER PUBLICATIONS

Proctor et al. CAS: 104: 2695, 1985.*
Christensen et al., "Megalin and Cubilin: Multifunctional Endocytic Receptors", Nature, vol. 3, Apr. 2002, pp. 258-268.
Haptoglobin intravenous injection 2000 unit JB Medical product Interview Form p. 6 (*Please see paragraphs [0008]-[0011] of the present application as filed, which provides a concise explanation of relevance*).
Hori et al., "Megalin Blockade with Cilastatin Suppresses Drug-Induced Nephrotoxicity", Journal of the American Society of Nephrology, vol. 28, 2017, pp. 1783-1791.
International Search Report (with English translation) for PCT/JP2022/010031, mailed on Apr. 19, 2022, 4 pages.
Rubio-Navarro et al., "Podocytes are new cellular targets of haemoglobin-mediated renal damage", Journal of Pathology, vol. 244, pp. 296-310.
Zagar et al., "An evaluation of the antioxidant protein al-microglobulin as a renal tubular cytoprotectant", American Journal of Physiology-Renal Physiology, vol. 311, 2016, pp. F640-F651.
Japanese Decision to Grant a Patent (with English translation) for Japanese Patent Application No. 2023- 505580, drafting date Nov. 13, 2023, 3 pages.
Japanese Notice of Reasons for Refusal (with English translation) for Japanese Patent Application No. 2023-505580, drafting date Jul. 5, 2023, 5 pages.
Assmann et al., "The organ distribution of gp-330 (Heymann antigen) and gp-90 in the mouse and the rat", Virchows Arch A Pathol Anat Histopathol, vol. 408, 1986, pp. 541-553.
Cheng et al., "Crystal structures of the extracellular domain of LRP6 and its complex with DKK1", Nature Structural & Molecular Biology, vol. 18, 2011, 20 pages.
Dagil et al., "Gentamicin Binds to the Megalin Receptor as a Competitive Inhibitor Using the Common Ligand Binding Motif of Complement Type Repeats", The Journal of Biological Chemistry, vol. 288. No. 6, Feb. 8, 2013, pp. 4424-4435.
Dvanajscak et al., "Hemolysis-associated hemoglobin cast nephropathy results from a range of clinicopathologic disorders", Kidney International, vol. 96, 2019, pp. 1400-1407.
Kerjaschki et al., "Identification of a 400-kd Protein in the Brush Borders of Human Kidney Tubules That Is Similar to gp330, the Nephritogenic Antigen of Rat Heymann Nephritis", American Journal of Pathology, vol. 129, No. 1, Oct. 1987, pp. 183-191.
Mori et al., "Increase of Total Nephron Albumin Filtration and Reabsorption in Diabetic Nephropathy", J Am Soc Nephrol, vol. 28, 2017, pp. 278-289.
Ni et al., "Allosteric Modulators of Protein-Protein Interactions (PPIs)", Protein Allostery in Drug Discovery, 2019, pp. 313-334.
Zheng et al., "Megalin (gp330): a putative endocytic receptor for thyroglobulin (Tg)", Abstract only, Endocrinology, vol. 139, No. 3, Mar. 1998, 1 page.
Chen, "Pathophysiology" (w/ Partial English Translation), Fudan University Press, 2015, 3 pages.
Extended European Search Report for corresponding Application No. 22767147.6, dated May 14, 2024, 9 pages.

(Continued)

*Primary Examiner* — Rei Tsang Shiao
(74) *Attorney, Agent, or Firm* — Dority & Manning, P.A.

(57) ABSTRACT

One object of the present invention is to provide an inhibitor for renal injuries induced by a hemolytic reaction. In this invention, cilastatin or a pharmaceutically acceptable salt thereof is used.

4 Claims, 4 Drawing Sheets

(56) References Cited

OTHER PUBLICATIONS

Van Avondt et al., "Mechanisms of haemolysis-induced kidney injury", Nature Reviews, Nephrology vol. 15, Nov. 2019, pp. 671-692.

* cited by examiner

Control (hemolysis model mice + normal saline)

Hemolysis model mice + cilastatin

Kidney tissues stained by an anti-hemoglobin antibody
Verification of inhibitory effect of CS on hemoglobin uptake in hemolysis model mice

Fig. 6

Control mice

α1M accumulation in renal tubule is found

Kidney-specific megalin KO mice

No α1M accumulation is found

Fig. 7

PREVENTION OF KIDNEY INJURY INDUCED BY HEMOLYTIC REACTION

CROSS REFERENCE TO RELATED APPLICATIONS

This application is the U.S. National Stage entry of International Application No. PCT/JP2022/010031 filed under the Patent Cooperation Treaty on Mar. 8, 2022, which claims priority to Japanese Patent Application No. 2021-040083 filed on Mar. 12, 2021, both of which are incorporated herein by reference.

TECHNICAL FIELD

The present invention relates to inhibition of renal injuries induced by a hemolytic reaction. More specifically, this invention relates to an inhibitor for renal injuries induced by a hemolytic reaction, the inhibitor comprising cilastatin or a pharmaceutically acceptable salt thereof. The present invention also relates to an inhibitor for hemoglobin or heme uptake into kidney tissues.

BACKGROUND ART

It is known that when a large amount of free hemoglobin is released into blood by a hemolytic reaction (hemoglobinemia), hemoglobin passing through the glomerulus is excreted in the urine (hemoglobinuria) causing injuries of renal tubular epithelial cells thereby leading to renal injuries.

One of the mechanisms of renal injuries currently presumed is that hemoglobin taken up into renal tubular epithelial cells produces reactive oxygen species through the iron contained in a heme and it causes cell injuries. Further, the heme freed from hemoglobin is known to be excreted in blood and urine, and it is thus believed that the free heme also causes injuries in renal proximal tubule.

It is said that the renal proximal tubular injuries caused by the hemoglobin, heme, and iron derived from hemolytic reaction trigger the renal tubular obstruction due to columnar shape cell components dropped out by the injuries, thereby leading to the onset of acute renal failure.

The hemolytic reaction occurs in various cases. The causes include, in addition to antibodies, genetic abnormality, and infectious diseases, mechanical causes such as cardiopulmonary bypass (CPB), extracorporeal membrane oxygenation (ECMO) or hemodialysis (HD), and ventricular assist device (VAD).

The renal injuries induced by the hemoglobin and heme derived from the hemolytic reaction cause the onset of acute kidney injury (AKI). AKI, in most cases, is transient and reversible but can be aggravated in some cases and seriously affects prognosis, and further transition from AKI to a chronic kidney disease is known in some cases. Further, in the case of developing AKI because of a medical procedure of some kind, AKI can possibly disturb the original therapy. For example, it is reported that the AKI incident frequency in the cases undergoing CPB is 18.2%, and the AKI incident frequency in the cases undergoing ECMO is 62.8%.

Thus, means for inhibiting renal injuries induced by the hemolytic reaction is in demand.

For the purpose of treating hemoglobinemia and hemoglobinuria, haptoglobin (Hp) products have been clinically applied. Hp, a plasma glycoprotein, has the characteristic of specifically binding to hemoglobin. Hp forms the Hp-hemoglobin complex in blood, and the Hp is presumed to transport free hemoglobin for its treatment to the liver without excreting the hemoglobin in the urine, thereby preventing the renal injuries caused by the free hemoglobin (NPL 1).

However, most of the Hp supply to be the product raw material relies on blood donation causing concerns for stable procurement into the future, and is expensive. For example, the drug price of the above Hp product in Japan in terms of the standard single dose based on the package insert is 88,752 in JP Yen (at the time of filing).

Additionally, Hp, a fractionated plasma product, fails to completely deny an infection risk with a pathogen when administered despite the countermeasure taken against pathogen contamination during the product formulation (NPL 1).

There is no report on the binding property between Hp and the free heme, and for this reason, the effect of Hp on the renal injuries induced by the hemolytic reaction is possibly limited.

In this regard, it is reported that $\alpha_1$-microglobulin ($\alpha_1 M$) and hemopexin (Hx), which are proteins produced in the liver, bind to a free heme and prevent reactive oxygen production (NPL 2). Additionally, it is also reported the use of recombinant hemopexin for the purpose of reducing the heme toxicity in hemolytic diseases (PTL 1). However, according to NPL 2, the heme-$\alpha_1 M$ complex possibly causes renal injuries when excessively taken up into kidney tissues.

It is reported that cilastatin can inhibit renal injuries caused by some drugs by antagonizing on the megalin receptor against the drugs binding to megalin, which is expressed in renal proximal tubular cells (NPL 3, PTL 2).

CITATION LIST

Patent Literature

PTL 1: Japanese Patent Translation of PCT International Application Publication No. 2017-531643
PTL 2: International Patent Publication No. WO2019/208777

Non Patent Literature

NPL 1: Haptoglobin intravenous injection 2000 unit "JB" Medical product Interview Form, page 6
NPL 2: Zagar et al., 2016, American Journal of Physiology-Renal Physiology, vol. 311, p. 640-651
NPL 3: Hori et al., Journal of the American Society of Nephrology, 2017, vol. 28, p. 1783-1791

SUMMARY OF INVENTION

Technical Problem

In one aspect of the present invention, an object of the present invention is to provide a novel means for inhibiting renal injuries induced by a hemolytic reaction.

In another aspect of the present invention, an object of the present invention is to provide a novel means for inhibiting hemoglobin or heme uptake into kidney tissues.

Solution to Problem

The present inventors have conducted intensive studies to achieve the aforementioned objects and as a result found that cilastatin ((Z)-7-[[(R)-2-Amino-2-carboxyethyl]thio]-2-[[[(S)-2,2-dimethylcyclopropyl]carbonyl]amino]-2-heptenoic acid) is effective to accomplish the aforementioned objects.

The present invention includes, but is not limited to, the following embodiments.
1. An inhibitor for renal injuries induced by a hemolytic reaction, comprising cilastatin or a pharmaceutically acceptable salt thereof as an active component.
2. The inhibitor according to 1, wherein the inhibitor is in an injectable form.
3. An inhibitor for hemoglobin uptake into kidney tissues, comprising cilastatin or a pharmaceutically acceptable salt thereof as an active component.
4. An inhibitor for heme uptake into kidney tissues, comprising cilastatin or a pharmaceutically acceptable salt thereof as an active component.

Advantageous Effects of Invention

The present invention can inhibit renal injuries induced by a hemolytic reaction.

It is considered that the hemoglobin freed by the hemolytic reaction is taken up into kidney tissues through the mediation of megalin and causes renal injuries. The present inventors confirmed that cilastatin inhibits the binding between megalin and hemoglobin and inhibits the hemoglobin uptake into kidney tissues. It is considered that the present invention inhibits renal injuries through this mechanism.

Additionally, the present inventors confirmed that $\alpha_1 M$ and Hx to which the heme freed from hemoglobin binds bind to megalin, and cilastatin inhibits the binding between $\alpha_1 M$ or Hx and megalin. Thus, the heme is intracellularly absorbed through the mediation of megalin and causes renal injuries, but it is confirmed that cilastatin inhibits the binding between $\alpha_1 M$ or Hx and megalin. For this reason, it is considered that cilastatin can inhibit the heme uptake into kidney tissues. It is then considered that the present invention can not only inhibit the injuries caused by the hemoglobin freed by the hemolytic reaction but also inhibit injuries caused by the heme.

The present invention is also advantageous in the aspects of safety and price. First of all, a combination agent of cilastatin and an antibiotic imipenem has been safely used for many years across the world. This verifies the safety of cilastatin. The drug price of the above combination agent (including the main agent) in Japan (in terms of the standard single dose based on the package insert) is 1,741 JP Yen.

As used herein in connection with renal injuries, the term "inhibit (inhibiting or inhibition)" refers to, for example, complete prevention of the onset of a symptom, or reduction of a symptom. The term "reduction" as referred to above includes decreasing the degree of the onset of the symptom, decreasing the symptom occurred, and complete elimination of the symptom occurred. Herein, complete prevention of the onset or reduction of the degree of the onset of a disease symptom is referred to as "prevention". Further, a medicament for "inhibiting" may also be referred to as an "inhibitor".

These acknowledgements in respect of the "inhibition" also apply mutatis mutandis to the "inhibition" of uptake.

BRIEF DESCRIPTION OF DRAWINGS

FIG. 2-1 shows, using the quartz crystal microbalance (QCM) method, the binding property of megalin onto the hemoglobin- or Hx-immobilized quartz crystal sensor, and the inhibitory effect of cilastatin.

FIG. 2-2 shows, using the QCM method, the binding property of $\alpha_1 M$ onto the megalin-immobilized quartz crystal sensor, and the inhibitory effect of cilastatin.

DESCRIPTION OF EMBODIMENTS

Renal Injuries Induced by Hemolytic Reaction

In one aspect, the present invention is directed to an inhibitor for renal injuries induced by a hemolytic reaction.

The hemolytic reaction which causes renal injuries include congenital causes and acquired causes. Examples of the congenital causes include genetic abnormality associating with the red blood cell membrane, genetic abnormality associating with a red blood cell enzyme, and genetic abnormality of hemoglobin.

Examples of the acquired causes include antibodies to red blood cells such as autoantibody, maternal antibody in a newborn baby, and antibody from incompatible blood transfusion, protozoan or bacterial infections, paroxysmal nocturnal hemoglobinuria, liver diseases, hypophosphatemia, and snake venom.

Examples of the cases where the present invention is considered to be particularly frequently used include renal injuries induced by the hemolytic reactions caused by physical red blood cell destruction, such as valvular disease of the heart and cardiac valve replacement, hemolytic uremic syndrome, march hemoglobinuria, heat or fire burns, blood purification therapies such as massive blood transfusion, CPB, ECMO, VAD, or HD.

When the above backgrounds or causes are present, the hemolytic reaction may have been occurred. The inhibitor of the present invention can be prescribed when the hemolytic reaction is diagnosed to have occurred, or suspected to have occurred. The hemolytic reaction can be diagnosed or suspected to have occurred when, for example, clinical examinations have findings of reticulocytosis, an elevated serum indirect bilirubin level, an increased urobilinogen level in feces and urea, an increased plasma free hemoglobin level, a decreased serum haptoglobin level, or hemoglobinuria.

Further, in the case where the onset of renal injuries by the hemolytic reaction is concerned, particularly in subjects with a reduced renal function, the inhibitor can be prescribed as prevention.

Additionally, examples of inhibition of renal injuries induced by the hemolytic reaction concerned at clinical sites include, in terms of clinical examinations, inhibition of an elevated serum creatinine level, a reduced renal filtration function (GFR, eGFR), an elevated blood urea nitrogen level, an elevated blood uric acid level, or ion concentration abnormality in blood or urea, and also inhibition of urinary concentration abnormality of, so-called renal injury markers, KIM-1, N-acetyl-β-D-glucosaminidase (NAG), $\alpha_1 M$, β2-microglobulin (β2M), Liver-type Fatty Acid-Binding Protein (L-FABP), Neutrophil Gelatinase-Associated Lipocalin (N-GAL), albumin (ALB), type IV collagen, megalin, or podocalyxin.

Additionally, examples of inhibition of renal injuries from a viewpoint of clinical symptoms include inhibition of edema, hypertension, uremia symptoms (nausea and vomiting, consciousness disturbance and the like), or jaundice, inhibition of appearance of hematuria, hemoglobinuria, or proteinuria, or inhibition of reduction in urine volume, and examples of inhibition of renal injuries from a pathological viewpoint include inhibition of renal tubular epithelial injuries, cast formation, renal tubular obstruction, stromal cell infiltration/edema/fibrosis, glomerular injury, or angiopathy.

These renal injuries can be induced through the mediation of megalin. Since the main site of expression of megalin in the body is renal proximal tubular epithelial cells (mainly luminal plasmalemma), the present invention is useful for the inhibition (i.e., as an inhibitor) of renal proximal tubular epithelial cell injury and renal injuries derived therefrom.

Examples of renal injuries induced by the hemolytic reaction include nephropathy, renal injury, nephritis, renal failure, renal disease, acute nephropathy, acute kidney injury, acute nephritis, acute renal failure, acute renal disease, chronic nephropathy, chronic renal injury, chronic nephritis, chronic renal failure, chronic kidney disease, tubular nephropathy, tubular renal injury, tubular nephritis, tubular renal failure, tubular renal disease, tubulointerstitial nephropathy, tubulointerstitial renal injury, tubulointerstitial nephritis, tubulointerstitial renal failure, tubulointerstitial renal disease, obstructive nephropathy, obstructive renal injury, obstructive nephritis, obstructive renal failure, obstructive renal disease, acute nephritic syndrome, rapidly progressive nephritic syndrome, chronic nephritic syndrome, nephrotic syndrome, renal vasospasm, and acute tubular necrosis.

Cilastatin

In the present invention, cilastatin or a pharmaceutically acceptable salt thereof is used.

Cilastatin refers to (Z)-7-[[(R)-2-Amino-2-carboxyethyl] thio]-2-[[[(S)-2,2-dimethylcyclopropyl]carbonyl]amino]-2-heptenoic acid. For the sake of confirmation, when cilastatin produces a hydrate, use of the hydrate is also included within the scope of this invention.

Examples of a pharmaceutically acceptable salt of cilastatin include alkali metal salts, such as lithium salt, sodium salt and potassium salt; alkali earth metal salts, such as magnesium salt and calcium salt; zinc salt and aluminum salt; organic amine salts, such as choline salt, ethanolamine salt, trimethylamine salt, triethylamine salt, dicyclohexylamine salt, dibenzylamine salt, phenethylbenzylamine salt, procaine salt, morpholine salt, pyridine salt, piperidine salt, piperadine salt and N-ethylpiperidine salt; ammonium salt; basic amino acid salts, such as lysine salt and arginine salt. A particularly preferred salt is cilastatin sodium. For the sake of confirmation, the scope of pharmaceutically acceptable salts also includes hydrates of the salts.

As cilastatin or a pharmaceutically acceptable salt thereof, use can be made of, for example, a commercially available product, or a product produced or obtained by a known method or by a method pursuant to a known method.

Cilastatin binds to the extracellular region of megalin. Cilastatin or a pharmaceutically acceptable salt thereof can inhibit the direct or indirect binding of hemoglobin and heme to megalin, and the uptake of them into cells.

The inhibitor of the present invention contains cilastatin or a pharmaceutically acceptable salt thereof in an effective amount for inhibiting renal injuries induced by the hemolytic reaction. In the case of renal injuries, an exemplary daily dose of cilastatin or a salt thereof in an adult is from 0.01 to 100 mg, or from 0.1 to 10 mg. To achieve a dose in such a range, the inventive inhibitor can be administered once or in divided doses. The inhibitor may also be administered using an intermittent dosing, such as alternate-day or every three day dosing.

Inhibitor for Hemoglobin Uptake into Kidney Tissues

The present invention, in an embodiment, relates to an inhibitor for hemoglobin uptake into kidney tissues, comprising cilastatin or a pharmaceutically acceptable salt thereof as an active component.

Hemoglobin is a protein present in red blood cells of vertebrates including human and has the tetramer structure composed of four subunits. In each subunit, the polypeptide moiety called globin and the heme moiety, which is a prosthetic group, bind. Hemoglobin has the nature of binding to oxygen molecules, and plays a role of transporting oxygen from the lungs to the entire body.

In connection with the present invention, the present inventors found that cilastatin inhibits the binding between hemoglobin and megalin. It is considered that this inhibitory effect leads to inhibition of renal injuries induced by the hemolytic reaction.

The inhibitor of the present invention contains cilastatin or a pharmaceutically acceptable salt thereof in an effective amount. The effective amount can be determined by reference to the doses and the like as mentioned above in connection with the inhibitor for renal injuries of the present invention.

Inhibitor for Heme Uptake into Kidney Tissues

The present invention, in an embodiment, relates to an inhibitor for heme uptake into kidney tissues, comprising cilastatin or a pharmaceutically acceptable salt thereof as an active component.

The hemes are the partial structure constituting hemoglobin and can be released in the body by hemoglobin degradation.

While the heme binds to $\alpha_1 M$ or Hx, the present inventors confirmed that $\alpha_1 M$ and Hx bind to megalin, and cilastatin inhibits the binding between these and megalin. It is considered that this inhibitory effect leads to inhibition of renal injuries induced by the hemolytic reaction.

The inhibitor of the present invention contains cilastatin or a pharmaceutically acceptable salt thereof in an effective amount. The effective amount can be determined by reference to the doses and the like as mentioned above in connection with the inhibitor for renal injuries of the present invention.

Dosage Form

The form of the inhibitor of the present invention is not particularly limited, and the inhibitor of this invention can be in the form of, for example, a solid formulation such as powder, granule, capsule, tablet or chewable tablet, a liquid formulation such as solution or syrup, or an injectable, or a spray. A preferred form is an injectable.

Other Components

The inhibitor of the present invention may contain a pharmaceutically acceptable carrier when required for pharmaceutical purposes. Examples of such a carrier include excipient and solvent. Examples of additional components that may be contained in the inhibitor of this invention include binder, pH adjustor, disintegrant, chelator, solubilizer, suspending agent, emulsifier, isotonic agent, stabilizer, soothing agent, antiseptic, antioxidant, lubricant, corrigent, and colorant.

Examples of excipients include organic excipients, such as sugars like lactose, glucose and D-mannitol, starches, and celluloses like crystalline cellulose; and inorganic excipients, such as dicalcium phosphate, calcium carbonate and kaolin. Examples of solvents include purified water and normal saline. Examples of binders include pregelatinized starch, gelatin, gum Arabic, methylcellulose, carboxymethylcellulose, carboxymethylcellulose sodium, crystalline cellulose, D-mannitol, trehalose, hydroxypropylcellulose, hydroxypropylmethylcellulose, polyvinylpyrrolidone, and polyvinyl alcohol. Examples of pH adjustors include hydrochloric acid and sodium hydroxide. Examples of disintegrants include low-substituted hydroxypropylcellulose, chemically modified celluloses and starches, and alginic acid. Examples of chelators include calcium disodium edetate hydrate and calcium sodium edetate hydrate. Examples of solubilizers include polyethylene glycol, propylene glycol, trehalose, benzyl benzoate, ethanol, sodium carbonate, sodium citrate, sodium salicylate and sodium acetate. Examples of suspending agents or emulsifiers include sodium lauryl sulfate, gum Arabic, gelatin, lecithin, glyceryl monostearate, polyvinyl alcohol, polyvinylpyrrolidone, celluloses like carboxymethylcellulose sodium, polysorbates, and polyoxyethylene hydrogenated castor oil. Examples of isotonic agents include sodium chloride, potassium chloride, sugars, glycerin, and urea. Examples of stabilizers include polyethylene glycol, sodium dextran sulfate, and other amino acids. Examples of soothing agents include glucose, calcium gluconate and procaine hydrochloride. Examples of antiseptics include p-hydroxybenzoic esters, chlorobutanol, benzyl alcohol, phenethyl alcohol, dehydroacetic acid, and sorbic acid. Examples of antioxidants include sulfite and ascorbic acid.

In a preferred embodiment, the inhibitor of the present invention does not contain imipenem.

Method and Use

In another aspect, the inhibitor of the present invention is directed to use of cilastatin or a pharmaceutically acceptable salt thereof in the inhibition of renal injuries induced by the hemolytic reaction, the inhibition of hemoglobin uptake into kidney tissues, or the inhibition of heme uptake into kidney tissues.

In another aspect, the inhibitor of the present invention is directed to a method for inhibiting renal injuries induced by the hemolytic reaction, inhibiting hemoglobin uptake into kidney tissues, or heme uptake into kidney tissues, the method comprising administering an effective amount of cilastatin or a pharmaceutically acceptable salt thereof to a subject in need thereof.

The effective amount of cilastatin or a pharmaceutically acceptable salt thereof can be determined by reference to the doses and the like as mentioned above in connection with the inhibitor of the present invention.

In a preferred embodiment, the method and use of the present invention do not comprise administration of imipenem.

The subject in need of various inhibitions herein is preferably a mammal such as human, a domestic animal such as mouse, rat, rabbit, guinea pig, hamster, monkey, sheep, horse, cow, pig, donkey, dog or cat, or other laboratory animal, with a human being particularly preferred.

Numerical Range

For the sake of clarity, the numerical ranges defined herein by lower and upper limit values, like "from 1.0 to 2.0 g", include the lower and upper limit values.

Examples

Hereunder, the present invention will be described by way of examples, but this invention is not limited to these examples.

(Test Example 1) Inhibition of Renal Injuries Induced by the Hemolytic Reaction by Cilastatin Blood urea nitrogen and urinary Kidney Injury Molecule-1 (KIM-1), renal injury indicators, were measured to verify whether the onset of renal injuries in hemolysis model mice is inhibited by cilastatin administration.

Method

Phenylhydrazine (97% phenylhydrazine, Sigma-Aldrich Inc.) was dissolved in PBS in a concentration of 5 mg/ml to prepare a PBS solution, and the solution was intraperitoneally given to C57BL/6 mice (male, aged 10-12 weeks) so that the dose of phenylhydrazine was 1 mg/10 g, thereby constructing homolysis models.

To the hemolysis models, a) 400 mg/kg (diluted in 100 μL of normal saline) of cilastatin (Sigma-Aldrich Inc.), or b) 100 μL of normal saline was intraperitoneally administered at the time of phenylhydrazine dosing, 3 hours after the dosing, and 6 hours after the dosing. For each a) and b), 6 mice were used.

Then, for each individual in a) cilastatin-treated group and b) normal saline-treated group (control group), urine was pooled using a metabolic cage for 24 hours after phenylhydrazine dosing, and the obtained urine samples were collected. Additionally, 24 hours after phenylhydrazine dosing, blood was collected from the inferior vena cava of each animal, centrifuged for 30 minutes at 800 g to separate and collect serum.

The urine and serum were stored at −80° C. until analysis and measured for urinary KIM-1 and blood urea nitrogen. The measurements were conducted by Oriental Yeast Co., Ltd.

Results

Figure 1:
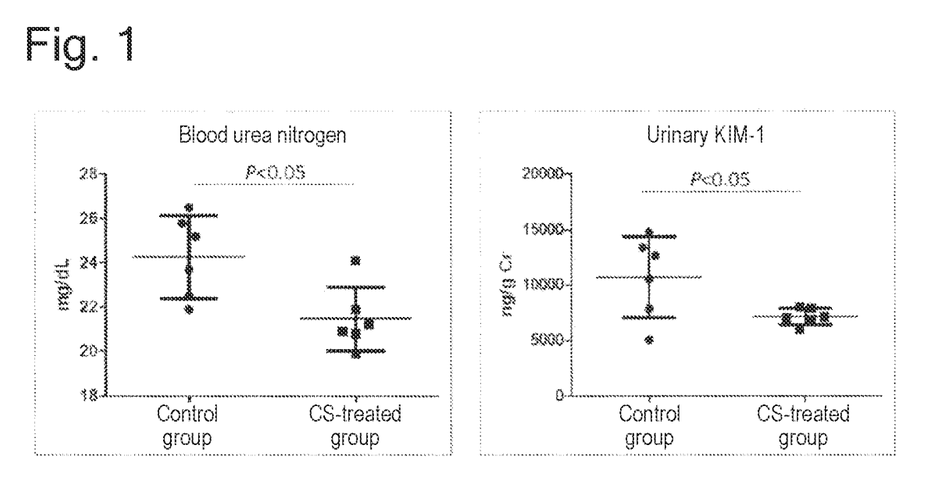
FIG. 1 shows the renal injury inhibitory effect of cilastatin in hemolysis model mice in terms of measured values of renal injury markers (blood urea nitrogen and urinary Kidney Injury Molecule-1: KIM-1).

As a result of evaluating renal injuries of the hemolysis models based on the blood urea nitrogen and urinary KIM-1, all measurement values were lower in the cilastatin (CS)-treated group than the control group (FIG. 1). It was found that renal injuries induced by the hemolytic reaction can be inhibited by cilastatin administration.

The present inventors consider as follows. The hemoglobin released by the hemolysis is taken up into kidney tissues through megalin and causes renal injuries. Further, the heme freed from the hemoglobin forms a complex by binding to $\alpha_1 M$ or Hx, and the complex is taken up into kidney tissues through megalin and causes renal injuries. Then, cilastatin inhibits the binding between the hemoglobin or the complex and megalin, and inhibits renal injuries. In the subsequent test examples, these action mechanisms of cilastatin will be confirmed.

(Test Example 2) Confirmation of the Action Mechanism (1)

Direct Binding Property Between Each Ligand and Megalin, and Binding Inhibition by Cilastatin Binding specificity between megalin and each ligand (hemoglobin, $\alpha_1 M$, Hx), and the possible binding inhibition by cilastatin were verified using the quartz crystal microbalance (QCM) method by reference to the method described in PTL 2.

Methodology-1

For the ligands to be verified, hemoglobin (LifeSpan Biosciences Inc., Rat Hemoglobin Native Protein, LS-G11201) and Hx (Sino Biological Inc., Rat Hemopexin/HPX protein (His Tag 81025-R08H)) were used.

With the use of an immobilization kit for AFFINIX® (Initium Inc.) according to the recommended protocol for the kit, each ligand solution prepared in Buffer A as provided with the kit to a concentration of 0.1 mg/mL, or a solution of bovine serum albumin (BSA: CALBIOCHEM, Albumin, Bovine Serum, Fraction V, Fatty Acid-Free, Cat #126575) as a control was placed on the quartz crystal sensor mounted in a holder, and the ligand or albumin was immobilized on the quartz crystal sensor.

After each of the ligand- or BSA-immobilized quartz crystal sensor was mounted in the measurement instrument AFFINIX® Q8 (Initium Inc.) and the frequency was confirmed to be stable, 8 μL of a 0.1 mg/mL solution of megalin purified from Sprague-Dawley (SD) rat kidneys according to the method of Orlando et al. was injected and frequency was measured with time.

More specifically, the megalin solution was reacted to each of the ligand-immobilized quartz crystal sensors placed in a chamber with 200 μL of buffer, and frequency was measured.

Additionally, 1 mg of cilastatin was injected into buffer in advance, each of the ligand-immobilized quartz crystal sensors was mounted in the measurement instrument, and after the frequency was confirmed to be stable, the megalin solution was injected and frequency was measured with time, whereby the antagonistic activity of cilastatin against the binding of each ligand to megalin was analyzed.

The same experiment was done on controls.

Methodology-2

In line with Methodology-1, a quartz crystal sensor on which a rat-purified megalin or BSA was immobilized was prepared. This quartz crystal sensor was mounted in the measurement instrument, and a condition under which 1 mg/200 μL of cilastatin was injected into buffer in advance and a condition under which cilastatin was not injected were set. After the frequency was confirmed to be stable, an $\alpha_1 M$ (LifeSpan Biosciences, Inc., Rat AMBP Protein (Recombinant 6His, N-terminus) (aa20-202), LS-G11794) solution was injected in an 8 μL chamber, and frequency was measured with time.

Results-1

Figure 21:
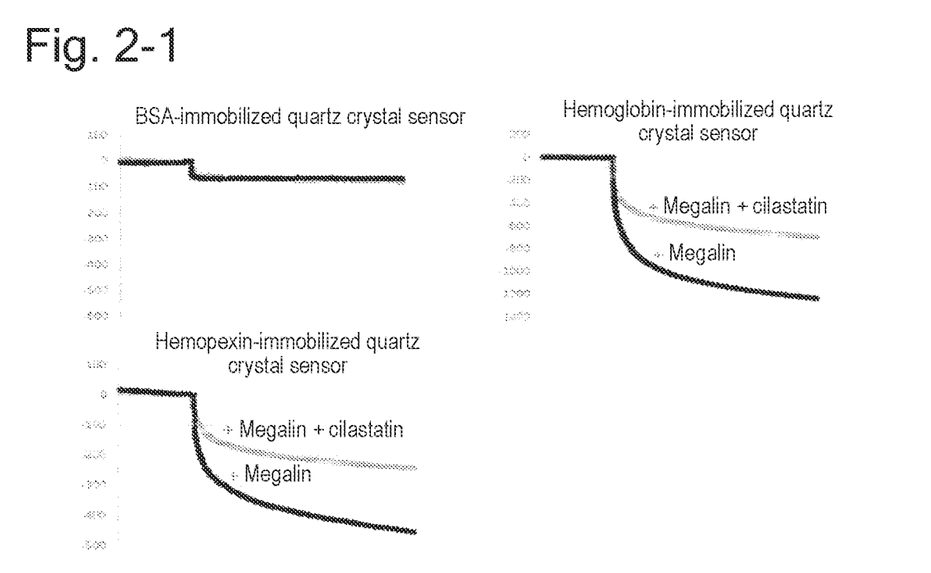

When megalin was added to the hemoglobin-immobilized quartz crystal sensor and the Hx-immobilized quartz crystal sensor, signals of the quartz crystal significantly dropped and this reaction was inhibited by cilastatin (FIG. 2-1). It was found that hemoglobin and Hx directly bind to megalin, and cilastatin inhibits such a binding.

Results-2

Figure 22:
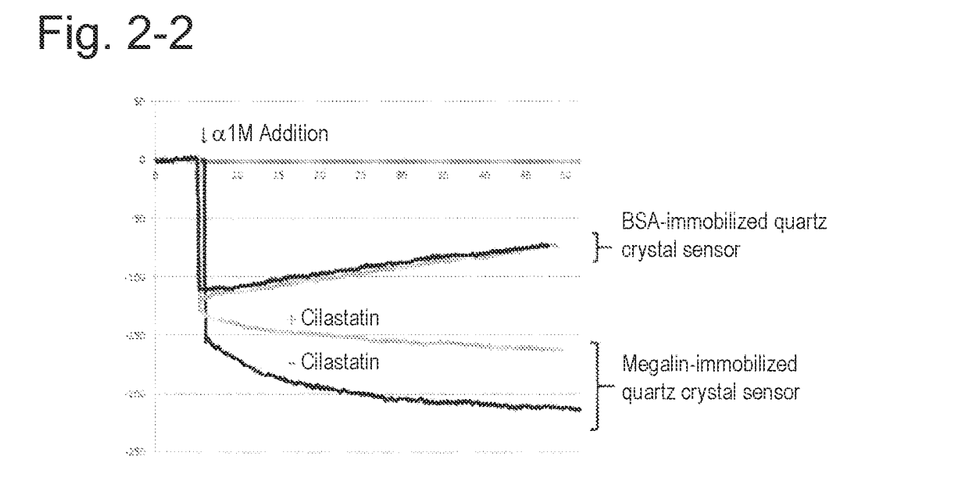

When $\alpha_1 M$ was added to the megalin-immobilized quartz crystal sensor, signals of the quartz crystal significantly dropped and this reaction was inhibited by cilastatin (FIG. 2-2). It was found that $\alpha_1 M$ directly binds to megalin as in hemoglobin and Hx, and cilastatin inhibits such a binding.

(Test Example 3) Confirmation of the Action Mechanism (2)

Relation of the Uptake of Each Ligand into Kidney Tissues and Megalin and Cilastatin This test example verified that each of the ligands ($\alpha_1 M$ and Hx) was taken up into kidney tissues through megalin, and cilastatin inhibits such an uptake.

Methodology

Cilastatin was administered to mice and changes in concentrations of each ligand in urine were observed.

Five mice (male, aged 12 weeks C57BL/6) were intraperitoneally administered with 400 mg/kg (diluted in 100 μL, of normal saline, cilastatin-treated group) of cilastatin sodium (Sigma-Aldrich Japan K.K., C5743), and then put in a metabolic cage for 3 hours to collect urine, and the urines of 5 mice were combined. Additionally, 100 μL, of normal saline was administered to another group of 5 mice (control group), and the same experiment as above was conducted.

Proteins were isolated from the obtained urine samples by electrophoresis (SDS-polyacrylamide gel), reductively alkylated (using dithiothreitol and iodoacetamide), digested with trypsin, and the obtained peptides were extracted to obtain a solid.

To the obtained solid, 15 μL, of 0.3% formic acid (FA) was added, shaken for 5 minutes, sonicated for 1 minute, and shaken again for 5 minutes. The resultant mixture was spun down, applied to a membrane filter having a pore diameter of 0.45 μm (ULtra free-MC, HV, 0.45 μm, Millipore), centrifuged at 10,000 rpm for 5 minutes, and the sample passed through the filter was subjected to LCMS analysis.

Analysis by LCMS

LC System

Eksigent® Exspert nano LC 400, Exsigent™ Exspert cHiPLC®

Column

Trap column: Nano cHiPLC Trap column 200 μm×0.5 mm ChromXP C18-CL 3 μm 120 Å (804-00006, SCIEX)

Analytical column: Nano cHiPLC column 75 μm×15 cm ChromXP C18-CL 3 μm 120 Å (804-00001, SCIEX)

Column temperature 30° C.

Sample Introduction

Injection volume: 3 μL

After holding the sample in a trap column, the gradient of mobile phase was adjusted as described later, and the sample was introduced to an analytical column.

Mobile Phase

A Solvent: Aqueous solution of 0.1% trifluoroacetic acid
B Solvent: Solution of 0.1% trifluoroacetic acid in acetonitrile Flow rate: Total 300 nl/min Gradient condition: When the sample was introduced to the analytical column equilibrated with 98% of A solvent and 2% of B solvent was 0 minute; the ratio of B solvent was linearly increased to 32% in 30 minutes; and the substance to be measured was separated and eluted. Subsequently, the ratio of B solvent was increased to 90% in 5 minutes; then the ratio of B solvent was retained at 90% for 5 minutes; the column was washed; the ratio was brought back to 2% in 0.1 minutes; and the ratio of B solvent was maintained at 2% as in the initial state until 60 minutes, thereby equilibrating the column.

Mass Spectrometer

AB Sciex Triple TOF 5600+ was used in positive ion mode.

TOF-MS Condition

Mass range: 400-1250 Da

Data Analysis

LCMS data were checked against the sequence database, and the presence of a plural proteins was confirmed. Moreover, the proteins confirmed in both of the cilastatin-treated group and control group were calculated for an SpC/L ratio (spectral abundance factor: SAF), which is equivalent to the peak intensity ratio of the cilastatin-treated group/control group, and those having an SpC/L ratio of 2.0 or more were decided to be proteins more abundant in urine of the cilastatin-treated group and listed as the proteins as such.

The analysis method described in Ohara et al., 2018, PLoS One, vol. 13, 1, e0204160 was referred to. The analysis method is shown below.

AnaLyst® TF1.6 (AB SCIEX) was used as an LCMS/MS data acquisition and analysis software, and the obtained raw data were converted to a peak list file (mgf file format), whereby MS/MS Ion Search (MIS search) was conducted using Matrix Science Mascot daemon, Mascot server 2.2.1. The sequence data base used was Uniprot, Swiss-Prot. Significance threshold was set to 0.05 (false discovery rate of less than 5%), and the proteins having 2 or more peptides exceeding the identification standard were listed as identified proteins.

Raw data were acquired 2 times per sample at LCMS to cover the issue of analysis reproducibility at LCMS, and the peak list files obtained from the 2 runs were combined and analyzed using Mascot (Ohara et al., 2018, PLoS One, vol. 13, 1, e0204160).

To the proteins identified in common in 2 groups when compared, the spectral count method was used, which is a label-free comparative, semiquantitative analysis method utilizing a principle that a large number of peptide fragments will be identified in those expressed at high levels, resulting in the increase in the number of MS/MS. In other words, the proteins identified in both of the cilastatin-treated group and control group were calculated for an SpC/L ratio (spectral abundance factor: SAF) of the cilastatin-treated group/control group, and the proteins having an SpC/L ratio of 2.0 or more were listed as the proteins abundant in urine of the cilastatin-treated group.

Urine Analysis by WB Using Anti-$\alpha_1$M Antibody

For the urines of the cilastatin-treated group and control group obtained in above, SDS-polyacrylamide electrophoresis under reduction condition was conducted using a 4 to 15% gradient gel (Bio-Rad Laboratories, Inc.), and developed fragments were transferred to a polyvinylidene fluoride (PVDF) membrane. The membrane was blocked using a 5% nonfat milk-containing buffer solution, and then reacted to 1 μg/mL of an anti-$\alpha_1$M antibody (LifeSpan Biosciences Inc.) as the primary antibody at room temperature for 2 hours. The membrane was reacted to 0.25 μg/mL of Polyclonal Goat Anti-Rabbit Immunoglobulin (Dako Japan Inc.) labelled with horseradish peroxidase (HRP) as the secondary antibody at room temperature for 1 hour. Subsequently, bands were detected using a western blot chemiluminescent substrate (SuperSignal™ West Femto Maximum Sensitivity Substrate, Thermo Scientific®).

Results

Figure 3:
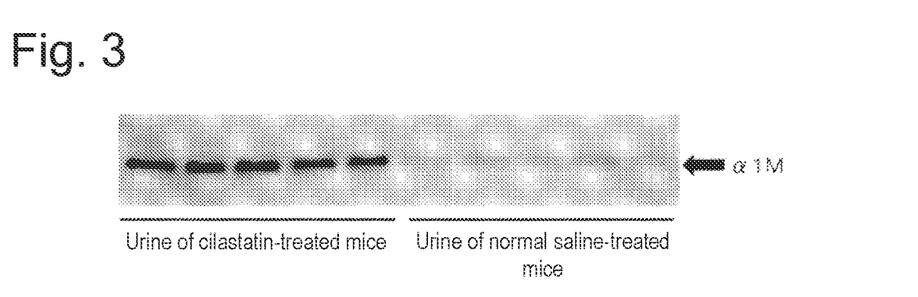
FIG. 3 shows the comparison of urinary protein ($\alpha_1$-microglobulin: $\alpha_1 M$) concentrations between the cilastatin-treated group and control group.

Of the proteins identified in both of the cilastatin-treated group and control group, 63 kinds having an SpC/L ratio of the cilastatin-treated group/control group of 2.0 or more were identified as the proteins with higher urinary concentrations in the cilastatin-treated group as compared to the control group. It is considered that the changes in urinary excretion of these proteins are affected by the megalin antagonistic activity by cilastatin. Further, in these, $\alpha_1$M and Hx, which are reported as the heme binders, were contained. As a reference, FIG. 3 shows western blotting images of urinary $\alpha_1$M in the cilastatin-treated group and control group.

Therefore, while it is reported that $\alpha_1$M is the ligand of megalin (Christensen et al., 2002, MOLECULAR CELL BIOLOGY, vol. 3, p. 258-268), the present study showed that Hx, not only $\alpha_1$M, is also the possible ligand of megalin. Additionally, it was confirmed that cilastatin inhibits the uptake of these into kidney tissues.

The proteins which did not change in the urinary concentrations in the cilastatin-treated group and control group contained those reported as megalin ligands such as albumin, transthyretin, clusterin, vitamin D-binding protein and the like. The present study showed that the binding, even it is a ligand of megalin, may not be antagonized by cilastatin.

Of the proteins having an SpC/L ratio of 2.0 or more and the proteins having an SpC/L ratio of less than 2.0 in the present test, the measured numerical values of examples of those already reported as ligands of megalin, or those found as ligands of megalin by the study of the present inventors are shown below.

TABLE 1

| Proteins having SpC/L ratio of 2.0 or more | |
| --- | --- |
| Protein name | SpC/L ratio |
| $\alpha_1$M | 3.67 |
| Hx | 2.33 |
| Transcobalamin-2 | 2.33 |

TABLE 2

| Proteins having SpC/L ratio of less than 2.0 | |
| --- | --- |
| Protein name | SpC/L ratio |
| Albumin | 1.10 |
| Transthyretin | 1.00 |
| Clusterin | 0.73 |
| Vitamin D-binding protein | 0.80 |

(Test Example 4) Confirmation of the Action Mechanism (3)

Megalin-Dependent Hemoglobin Uptake into Kidney Tissues

Megalin-dependency of the hemoglobin uptake into kidney tissues was verified using hemolysis models constructed from kidney-specific megalin-knock out (KO) mice.

Methodology

A solution of 5 mg/ml phenylhydrazine in PBS (97% phenylhydrazine, Sigma-Aldrich Inc.) was prepared, and an amount equivalent to 1 mg/10 g of the phenylhydrazine was intraperitoneally given to the kidney-specific megalin-KO mice (Ndrg1-CreERT2/+ megalin lox/lox) and control mice thereof (megalin (lox/lox); Cre(−)) as the control (both male, aged 12 weeks), thereby constructing hemolysis models.

Twenty-four hours after phenylhydrazine dosing, a portion containing a renal pedicle was sliced to 3 mm thickness from the right kidney and fixed with 4% paraformaldehyde phosphate buffer. The fixed sample was thinly sliced at a thickness of 4 μm using a microtome (REM-710; Yamato Kohki Industrial Co., Ltd.), and the obtained thin slices were immunostained (500-fold diluted) with an anti-hemoglobin antibody (Abcam ab92492) and microscopically observed.

Results

Figure 4:
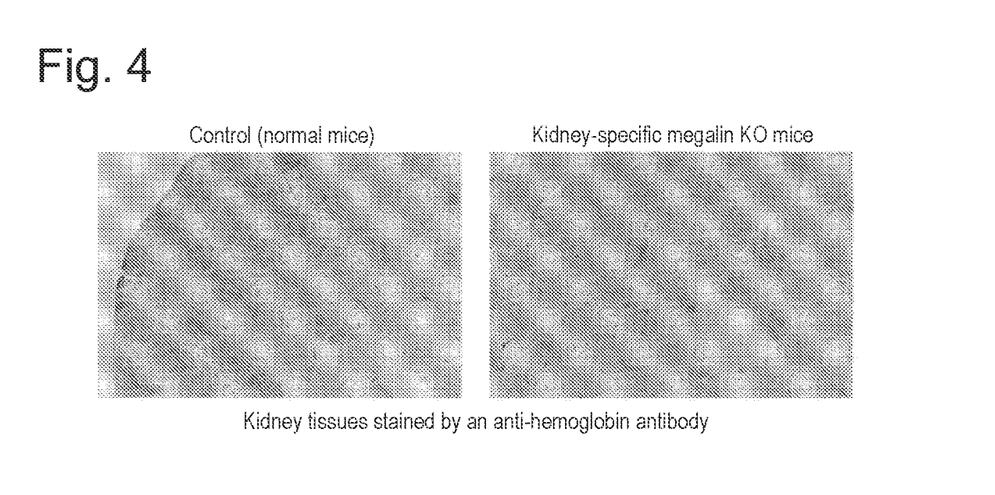
FIG. 4 shows the images comparing the amounts of hemoglobin taken up into kidney tissues between hemolysis models using kidney-specific megalin KO mice and control mice (immunostaining by anti-hemoglobin antibody).

It was confirmed that the amounts of hemoglobin taken up into kidney tissues of the hemolysis model mice were smaller in the megalin KO mice than in the control mice (FIG. 4). Therefore, it was found that the hemoglobin uptake into kidneys was dependent on megalin.

(Test Example 5) Confirmation of the Action Mechanism (4)

Inhibition of the Hemoglobin Uptake into Kidney Tissues by Cilastatin

The inhibition of hemoglobin uptake into kidney tissues by cilastatin administration was verified using hemolysis model mice.

Methodology

In line with Test Example 1, 1 mg/10 g of phenylhydrazine was given to C57BL/6 (male, aged 10-12 weeks), thereby constructing hemolysis model mice.

To the hemolysis models, a) 400 mg/kg (diluted in 100 μL, of normal saline) of cilastatin (Sigma-Aldrich Inc.), or b) 100 μL, of normal saline was intraperitoneally administered at the time of phenylhydrazine dosing, 3 hours after the dosing, and 6 hours after the dosing.

Twenty-four hours after phenylhydrazine dosing, kidneys were immunostained and observed by following Test Example 4.

Results

Figure 5:
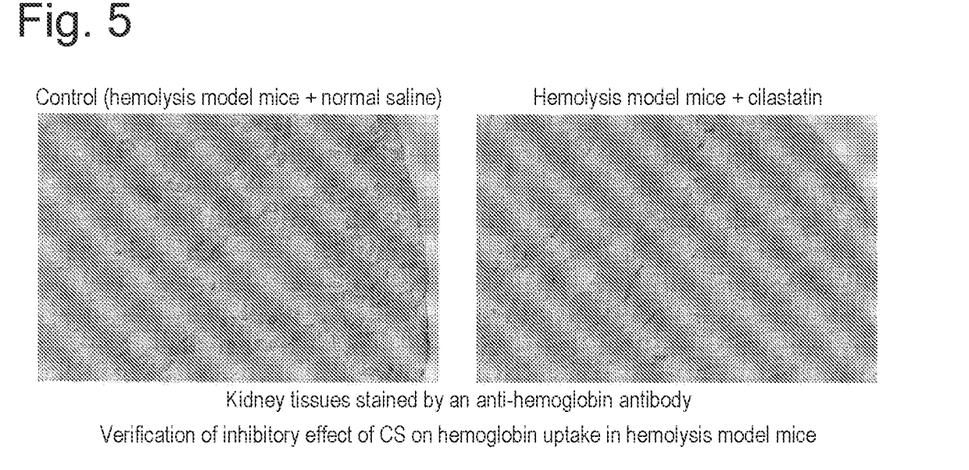
FIG. 5 shows the hemoglobin uptake inhibitory effect by cilastatin in hemolysis model mice (immunostaining by anti-hemoglobin antibody).

It was confirmed that the amounts of hemoglobin taken up into kidney tissues of the hemolysis model mice reduced by cilastatin administration (FIG. 5). Therefore, it was found that the hemoglobin uptake into kidneys can be inhibited by cilastatin.

(Test Example 6) Confirmation of the Action Mechanism (5)

Megalin-Dependent $\alpha_1$M Uptake into Kidney Tissues

Megalin-dependency of the $\alpha_1$M uptake into kidney tissues was verified using hemolysis models constructed from kidney-specific megalin-knock out (KO) mice.

Methodology

In Test Example 4, the thinly sliced fixed kidney samples were obtained, immunostained, and observed. In the present test example, separate thinly sliced fixed samples obtained from the remaining right kidney of the same animal were immunostained (500-fold diluted) using an anti-$\alpha_1$M antibody (Gene Tex: GTX101068) and microscopically observed.

Results

Figure 6:
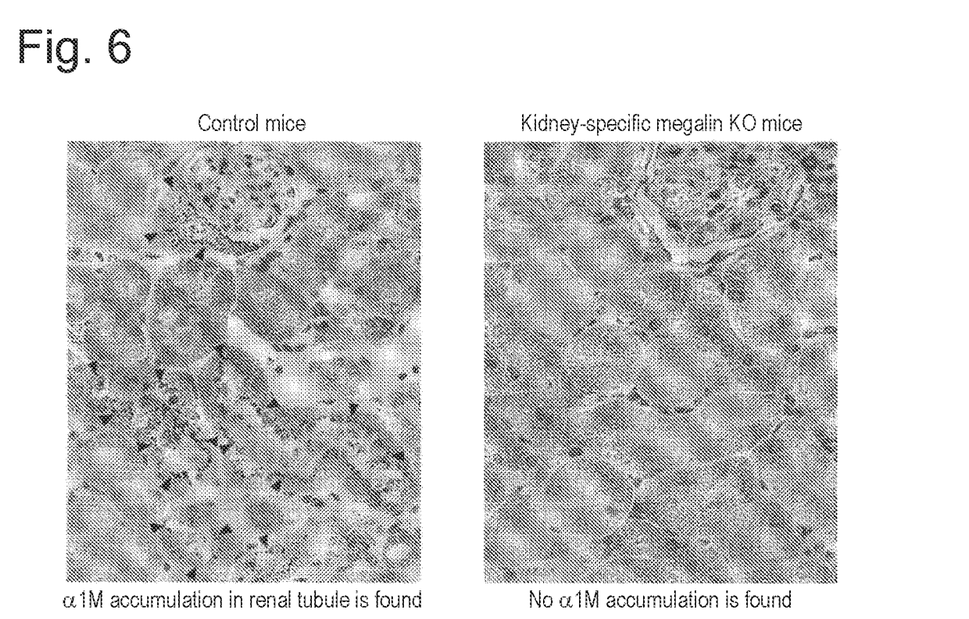
FIG. 6 shows the images comparing the amounts of $\alpha_1 M$ taken up into kidney tissues between hemolysis models using kidney-specific megalin KO mice and control mice (immunostaining by anti-$\alpha_1 M$ antibody).

It was confirmed that the amounts of $\alpha_1$M taken up into kidney tissues of the hemolysis model mice were smaller in the megalin KO mice than the control mice (FIG. 6). Therefore, it was found that the $\alpha_1$M uptake into kidney was dependent on megalin.

(Test Example 7) Confirmation of the Action Mechanism (6)

Inhibition of $\alpha_1$M Uptake into Kidney Tissues by Cilastatin

The inhibition of $\alpha_1$M uptake into kidney tissues by cilastatin administration was verified using hemolysis model mice.

Methodology

In Test Example 5, the thinly sliced fixed kidney samples were obtained, immunostained, and observed. In the present test example, thinly sliced fixed samples obtained from the remaining right kidney of the same animal were immunostained (500-fold diluted) using an anti-$\alpha_1$M antibody (Gene Tex: GTX101068).

Results

Figure 7:
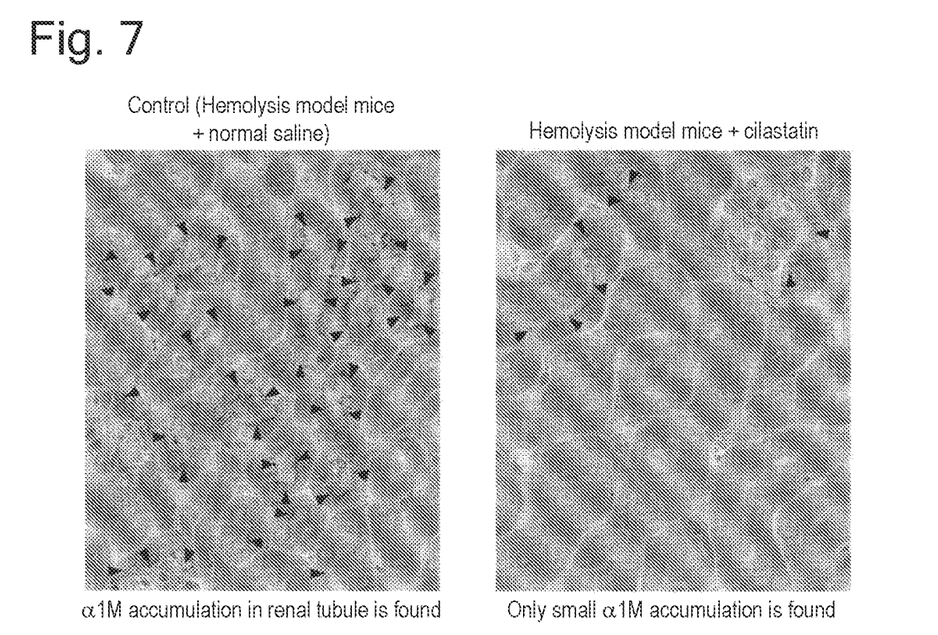
FIG. 7 shows the $\alpha_1 M$ uptake inhibitory effect by cilastatin in hemolysis model mice (immunostaining by anti-$\alpha_1 M$ antibody).

It was confirmed that the amounts of $\alpha_1$M taken up into kidney tissues of the hemolysis model mice reduced by cilastatin administration (FIG. 7). Therefore, it was found that the $\alpha_1$M uptake into kidneys can be inhibited by cilastatin.

INDUSTRIAL APPLICABILITY

The present invention is capable of providing an inhibitor for renal injuries induced by a hemolytic reaction, or an inhibitor for hemoglobin or heme uptake into kidney tissues.

The invention claimed is:

1. A method for inhibiting renal injuries induced by a hemolytic reaction, comprising administering to a subject in need thereof an inhibitor comprising cilastatin or a pharmaceutically acceptable salt thereof as an active component.

2. The method according to claim 1, wherein the inhibitor is in an injectable form.

3. A method for inhibiting hemoglobin uptake into kidney tissues, the method comprising administering to a subject in need thereof an inhibitor comprising cilastatin or a pharmaceutically acceptable salt thereof as an active component.

4. A method for inhibiting heme uptake into kidney tissues, comprising administering to a subject in need thereof an inhibitor comprising cilastatin or a pharmaceutically acceptable salt thereof as an active component.

* * * * *